(12) United States Patent
Oh

(10) Patent No.: US 8,463,367 B2
(45) Date of Patent: Jun. 11, 2013

(54) APPARATUS FOR MEASURING BIOLOGICAL INFORMATION AND EARPHONE HAVING THE SAME

(75) Inventor: Jung-Taek Oh, Seoul (KR)

(73) Assignee: Samsung Electronics Co., Ltd (KR)

( * ) Notice: Subject to any disclaimer, the term of this patent is extended or adjusted under 35 U.S.C. 154(b) by 668 days.

(21) Appl. No.: 12/634,376

(22) Filed: Dec. 9, 2009

(65) Prior Publication Data

US 2010/0152557 A1    Jun. 17, 2010

(30) Foreign Application Priority Data

Dec. 15, 2008  (KR) .................. 10-2008-0127461

(51) Int. Cl.
*A61B 6/00* (2006.01)
*A61B 5/00* (2006.01)

(52) U.S. Cl.
USPC .................... 600/478; 600/344; 600/310

(58) Field of Classification Search
USPC ........................................... 600/478
See application file for complete search history.

(56) References Cited

U.S. PATENT DOCUMENTS

| | | | |
|---|---|---|---|
| 6,080,110 A | 6/2000 | Thorgersen | |
| 7,209,775 B2 | 4/2007 | Bae et al. | |
| 2005/0014729 A1 | 1/2005 | Pulaski | |
| 2006/0260842 A1* | 11/2006 | Sim et al. | 174/562 |
| 2007/0063929 A1 | 3/2007 | Park et al. | |
| 2007/0183613 A1* | 8/2007 | Juneau et al. | 381/322 |
| 2007/0210242 A1 | 9/2007 | Cho | |
| 2008/0122661 A1 | 5/2008 | Han | |
| 2010/0298667 A1 | 11/2010 | Uenishi et al. | |

FOREIGN PATENT DOCUMENTS

| | | | |
|---|---|---|---|
| EP | 1 374 736 | | 1/2004 |
| KP | 1020080056950 | * | 6/2008 |
| KR | 1020060119007 | | 11/2006 |
| KR | 1020070092869 | | 9/2007 |
| KR | 100770883 | | 10/2007 |
| KR | 1020070095489 | | 10/2007 |
| KR | 1020080047902 | | 5/2008 |
| KR | 1020080056950 | | 6/2008 |
| WO | WO 2005/034742 | | 4/2005 |

\* cited by examiner

*Primary Examiner* — Tse Chen
*Assistant Examiner* — Patricia Park
(74) *Attorney, Agent, or Firm* — The Farrell Law Firm, P.C.

(57) ABSTRACT

Disclosed is an apparatus for measuring biological information and an earphone having the same for contacting with a uniform pressure a user body part using an elastic member. The apparatus includes a first housing; a second housing foldably connected with the first housing; a third housing foldably connected with the second housing and provided with a sensor for measuring the biological information; a plurality of joint parts for connecting the housings to be folded or unfolded to each other; one or more locking parts for restraining or releasing the housings to be folded or unfolded to each other; and the elastic member for applying the same pressure to make the sensor contact with the user's body by enabling the respective housings to be folded or unfolded using a stress-strain.

12 Claims, 10 Drawing Sheets

APPARATUS FOR MEASURING BIOLOGICAL INFORMATION AND EARPHONE HAVING THE SAME

PRIORITY

This application claims priority to an application entitled "Apparatus for Measuring Biological Information and Earphone Having the Same" filed in the Korean Industrial Property Office on Dec. 15, 2008 and assigned Ser. No. 10-2008-0127461, the contents of which is incorporated herein by reference.

BACKGROUND OF THE INVENTION

1. Field of the Invention

The present invention relates to an apparatus for measuring biological information and an earphone incorporating the apparatus having a sensor for measuring biological information by contact with a portion of a user's body.

2. Description of the Related Art

Measurement of biological information obtained from blood streams of a human body, such as a pulse rate, a number of heartbeats or the like, is performed using a variety of conventional devices of a variety of shapes or sizes, often miniaturized in a portable size or incorporated into other products.

For example, a measuring apparatus is provided in which a pulse sensor is installed within a wristwatch. When a user touches the pulse sensor using an inner surface of his/her fingertip, the pulse sensor optically detects a pulse count, and the pulse rate is displayed of the wristwatch.

The conventional apparatus for measuring the biological information as described above will typically use an electrocardiogram (ECG) sensor designed to measure the pulse rate by detecting signals using a multi-polar electrode. Further, a photo sensor has been disclosed to measure the biological information that irradiates light onto a skin surface of the user's body via a Light Emitting Diode (LED) and detects reflected light, observing scattering of light within the user's body via a Photo Diode (PD).

WO/2005/034742, the contents of which are incorporated herein by reference, is an example of a conventional apparatus for measuring the biological information. When this apparatus is used as a sensor for measuring the pulse rate using a transmission-type photo sensor applied to an earlobe, the sensor is adapted to compress the earlobe using pincers, that typically include two arms, a pivot and a spring.

However, the conventional ECG sensor needs to employ an electrode made from a conductive material or a special pad on which a high viscosity material, such as a gel, is applied. In addition, in order to perform a test while the user is exercising, the conventional ECG sensor must be installed on the user's body in a location, such as the chest, where muscles move. Further, it is difficult to obtain the number of heartbeats due to the disturbance of the ECG signals by the electromyogram (EGM) signal.

Special clothing, such as a bio-shirt, has been developed for use when tests are performed during exercise. However, use of such special clothing is inconvenient.

In order to solve the drawbacks described above, studies have been published for miniaturizing measuring devices for collecting biological information. As a result, an apparatus which can be mounted on an earphone using the structure of the user's ear has been developed.

When the apparatus for measuring the biological information is installed on the earphone, the apparatus adopts a measuring method to check the biological information with a transmission-type sensor positioned in an earflap of the user. However, such apparatus has drawbacks in that a significant amount of noise is generated by relative movement of the earphone against the user's skull. However, this relative movement is difficult to prevent due to the physical proximity of the earlobe to the skull and the weight of the earphone.

To solve the problems caused by the relative movement due to the weight of the earphone as described above, a lightweight chip of a sensor part is separated from the apparatus when the apparatus is in use. However, such construction is inconvenient in that the user must additionally care for the lightweight chip. A method to mount the chip in the earlobe of the user has also been proposed, but is structurally complicated due to its construction using a heavy earphone and an additional chip, making transport of the apparatus inconvenient.

As another way of solving the above drawbacks, an apparatus is provided in which the sensor part is completely inserted in the user's ear. Such apparatus, however, has disadvantages in that the user cannot listen to music because the apparatus interferes with an earphone function.

The above-described pincer-type apparatus is inconvenient to use since the spring force will vary depending on thickness and length of a user's earlobe, and further it is very difficult to obtain exact measurements.

Moreover, more space is needed due to the configuration of the pincer-type, and there is a practical inconvenience for the user because opening operations of the pincers for inserting the sensor part are totally contradicted with operations for inserting the earphone, when the apparatus is incorporated with the earphone.

Hence, there is a need for an apparatus capable that accurately measures exact biological information by elimination of the pressure difference caused by thickness and length variations in user earlobes, allowing the sensor to contact the earlobe with uniform pressure.

SUMMARY OF THE INVENTION

Accordingly, the present invention has been made to solve the above-mentioned problems of conventional devices, and the present invention provides an apparatus for measuring biological information and an earphone having the same which can reduce a signal deviation of the biological information due to the difference in the thickness and length of the user's body part and obtain a signal in its optimal state. In the present invention, a sensor apparatus is provided that contacts the user's body part with a uniform pressure for measuring biological information.

The present invention provides an earphone including an apparatus for measuring biological information. The present invention is constructed from a reduced number of components, thereby facilitating lower cost manufacture, and can be installed within a small space.

Further, the present invention provides an apparatus for measuring biological information and an earphone having the same which allows a product to be conveniently operated by providing a locking part to restrain or release folding or unfolding operations of a housing with a sensor for measuring the biological information using an elastic member.

In accordance with an aspect of the present invention, there is provided an apparatus for measuring biological information, including a first housing; a second housing foldably connected with the first housing; a third housing foldably connected with the second housing and provided with a sensor for measuring the biological information; a plurality of joint parts provided between the respective housings for connecting the housings to be folded or unfolded to each other; one or more locking parts provided between the respective housings for restraining or releasing the housings to be folded or unfolded to each other; and an elastic member provided within the respective housings and joint parts, which applies a same pressure to make the sensor contact with the user's body by enabling the respective housings to be folded or unfolded using a stress-strain which tends to return to its initial state when the locking part is restrained or released.

BRIEF DESCRIPTION OF THE DRAWINGS

The above and other aspects, features and advantages of the present invention will be more apparent from the following detailed description taken in conjunction with the accompanying drawings, in which.

DETAILED DESCRIPTION OF THE PREFERRED EMBODIMENTS

Figure 1:
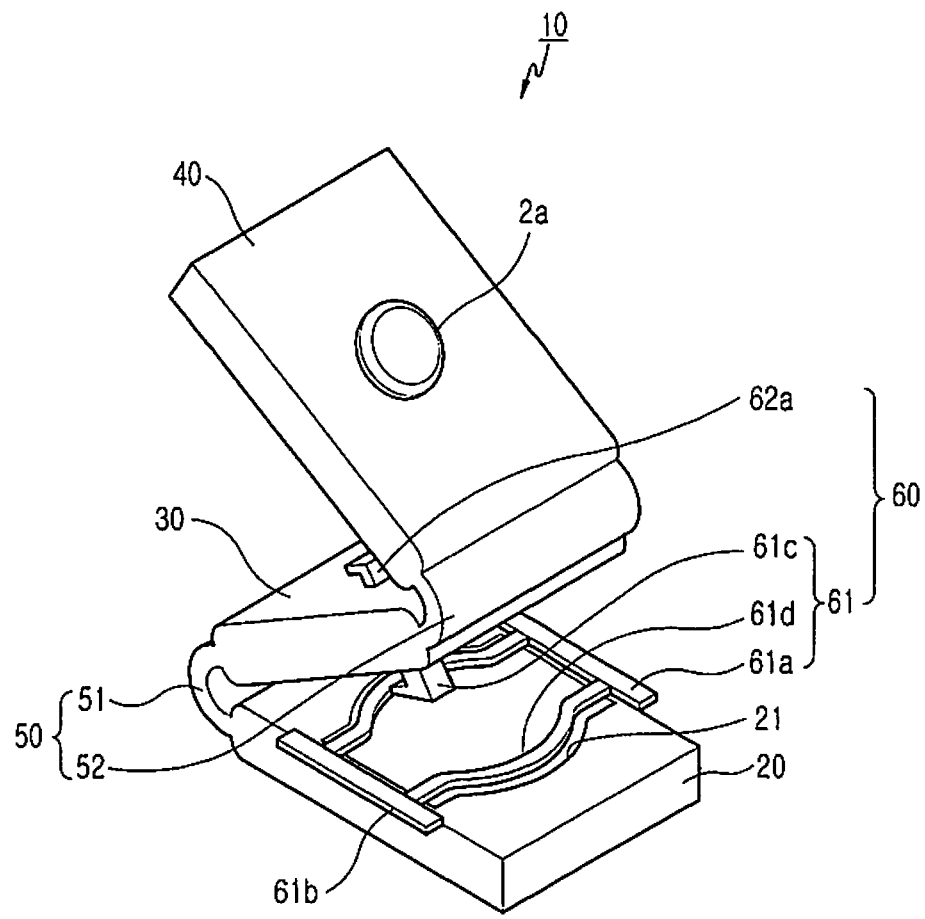
FIG. 1 is a perspective view illustrating the construction of an apparatus for measuring biological information in accordance with an embodiment of the present invention.

Hereinafter, exemplary embodiments of the present invention will be described with reference to the accompanying drawings. In the following description, the same elements will be designated by the same reference numerals although they are shown in different drawings. Further, various specific definitions found in the following description, such as specific values of packet identifications, contents of displayed information to provide a general understanding of the present invention. Further, in the following description of the present invention, a detailed description of known functions and configurations incorporated herein will be omitted when it may make the subject matter of the present invention rather unclear.

Figure 2A:
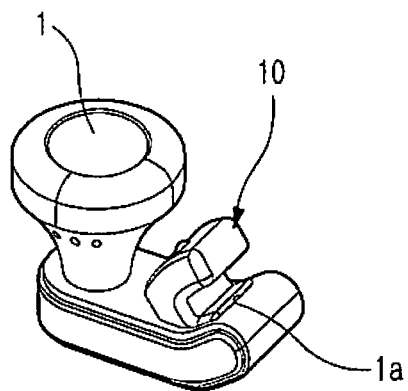
FIG. 2a is a perspective view illustrating a state in which the apparatus for measuring biological information installed in an earphone, in accordance with an embodiment of the present invention.
Figure 2B:
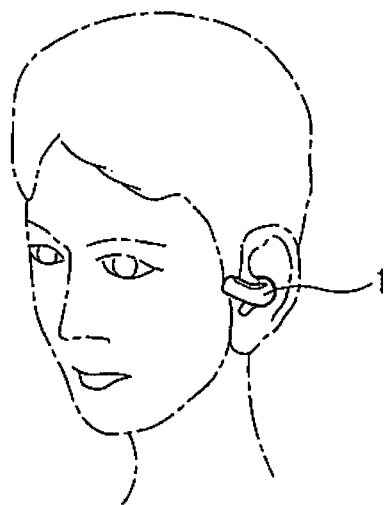
FIG. 2b is a perspective view of an embodiment of the present invention inserted in a user's ear.
Figure 2C:
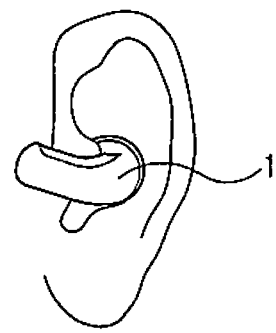
FIG. 2c is an enlarged perspective view illustrating the apparatus of FIG. 2b.
Figure 3:
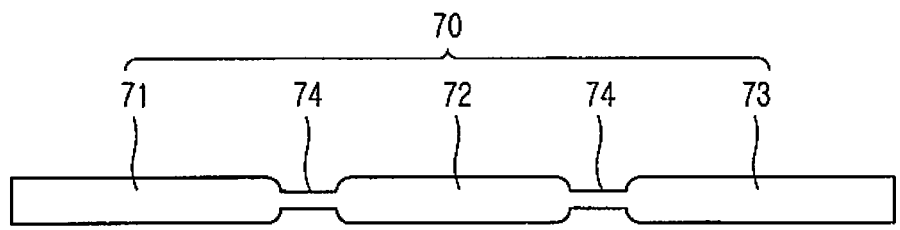
FIG. 3 is a top plan view illustrating an elastic member of the apparatus for measuring biological information in accordance with an embodiment of the present invention.
Figure 4A:
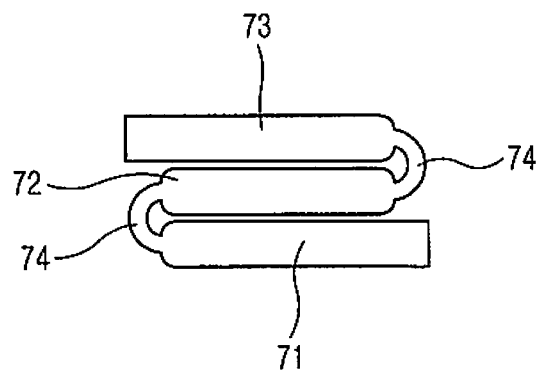
FIG. 4(a) shows the elastic member in a non-operating state.
Figure 4B:
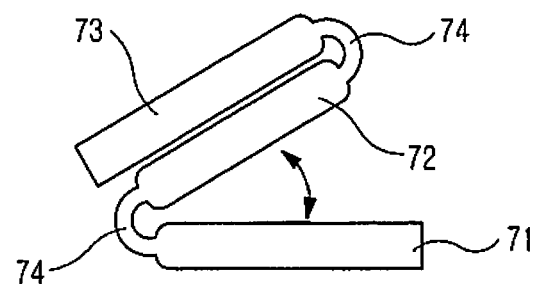
FIG. 4(b) shows the elastic member in an operating state.
Figure 4C:
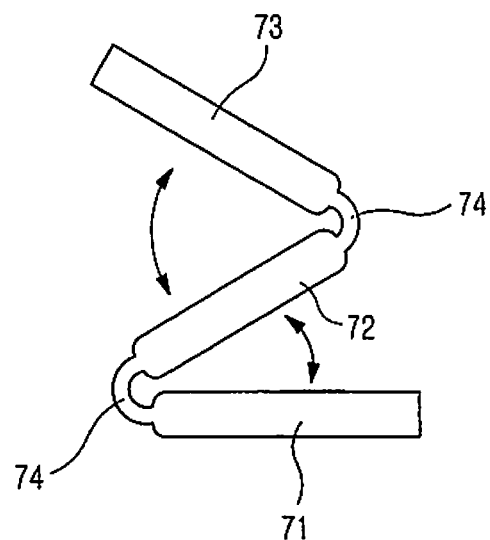
FIG. 4(c) shows the elastic member after operation.

Referring to FIGS. 1 through 7, an apparatus 10 for measuring biological information includes first, second and third housings, 20, 30 and 40, a plurality of joint parts 50, a locking part (FIGS. 1, 6 and 7), and an elastic member 70 (FIG. 3).

The first housing 20 is connected with one end of the second housing 30 so that the second housing 30 can be folded or unfolded against the first housing 20. The second housing 30 is connected with one end of the third housing 40 such that the third housing 40 can be folded or unfolded against the second housing 30. The third housing 40 is connected with the other end of the second housing 30 and provided with a Light Emitting Diode (LED) 2a of a sensor 2 (FIGS. 5(b)-5(d)) for measuring the biological information, when in contact with an earlobe of the user.

The joint parts 50 are provided between the first, second and third housings, 20, 30 and 40, which allow the first, second and third housings, 20, 30 and 40 to be foldably or unfoldably connected therewith, respectively. The locking part 60 is disposed between the first, second and third housings, 20, 30 and 40, to restrain or release the first, second and third housings, 20, 30 and 40 in a folded state. The elastic member 70 is provided within the respective first, second and third housings, 20, 30 and 40, and the joint parts 50, to apply a uniform pressure bringing the LED 2a into contact with the user's earlobe 3, and enable the respective housings 20, 30 and 40 to unfolded when the locking part 60 is released.

The apparatus 10 is applied to an earphone 1 as shown in FIGS. 2 and 5, and is applicable to a variety of other small electronic devices, such as an information transmission device, a multimedia device or the like which can be in contact with the user's body portion.

Referring to FIG. 2(a), the first housing 20 is installed in a mounting groove 1a formed in the earphone 1, which makes it possible for the user to listen to music as well as measure the number of his/her heartbeats.

As shown in FIG. 1, the joint parts 50 include first and second joint parts, 51 and 52, respectively. The first joint part 51 is provided between the respective ends of the first and second housings, 20 and 30, connecting the first housing 20 with the second housing 30 and enabling the second housing 30 to fold and unfold against the first housing 20. The second joint part 52 is provided between the respective ends of the second and third housings, 30 and 40, connecting the second housing 30 with the third housing 40 and enabling the folding and unfolding. The first and second joint parts 51 and 52 have smaller thickness than the respective housings 20, 30 and 40, facilitate folding and unfolding.

Referring to FIGS. 3 and 4(a) through 4(c), the elastic member 70 is designed to receive a constant force, and to be deformed up to about 8% of the strain.

As shown in FIGS. 1, 6, and 7, locking part 60 includes first and second locking parts 61 and 62, respectively. The first locking part 61 is provided between opposite facing sides of the first and second housings, 20 and 30, to restrain the first housing 20 to the second housing 30. When the user presses first and second pressing members, 61a and 61b, which are exposed outside of the first housing 20, the second housing 30 unfolds from the first housing 20.

The second locking part 62 is provided between opposite facing sides of the second and third housings, 30 and 40, to restrain the third housing 40 to the second housing 30. The second and third housings, 30 and 40, are retained by the first locking part 61.

Referring to FIGS. 6(a) to 6(d), the first locking part 61 includes the first and second pressing members 61a and 61b, a hook part 61c, and a pair of wire latch parts 61d. The first and second pressing members 61a and 61b are exposed outside of the first housing 20 and are designed to expand or shrink the pair of wire latch parts 61d by pressing down the first and second pressing members 61a and 61b. The hook part 61c is provided on one side of the second housing 30 to hook on one of the wire latch parts 61d and to release therefrom upon rotation of the second housing 30. One of the wire latch parts 61d is disposed at a location corresponding to the hook part 61c, and between the first and second pressing members 61a and 61b. A central portion of the wire latch parts 61d expands or shrinks in the opposite directions to hook or release the hook part 61c when the first and second pressing members 61a and 61b are pressed by the user. The hook part 61c is formed with a guide ramp 601 for helping one of the wire latch parts 61d smoothly engage the hook part 61c when the latter is brought into contact with the former.

The wire latch parts 61d are formed in a semi-sphere shape from a soft material to allow easy expansion or shrinking when pressed.

Figure 7A:
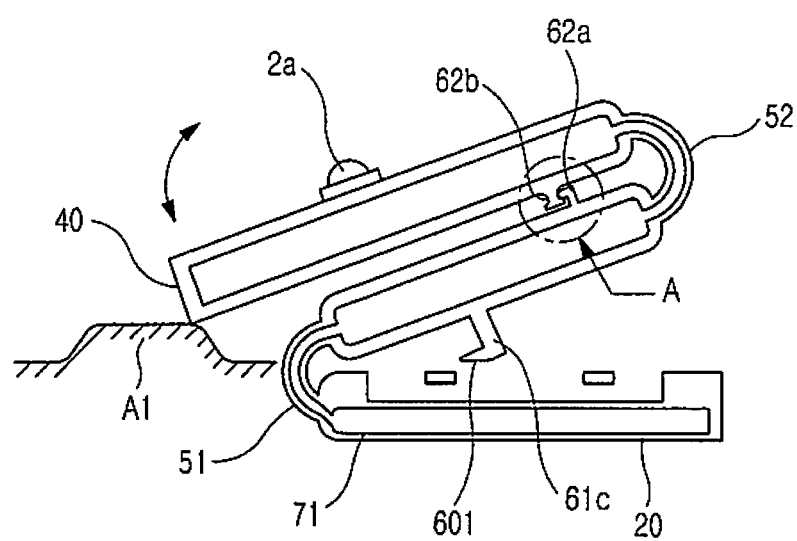
FIG. 7(a) is a sectional view of an embodiment of the present invention, wherein a second locking part is not yet operated.
Figure 7B:
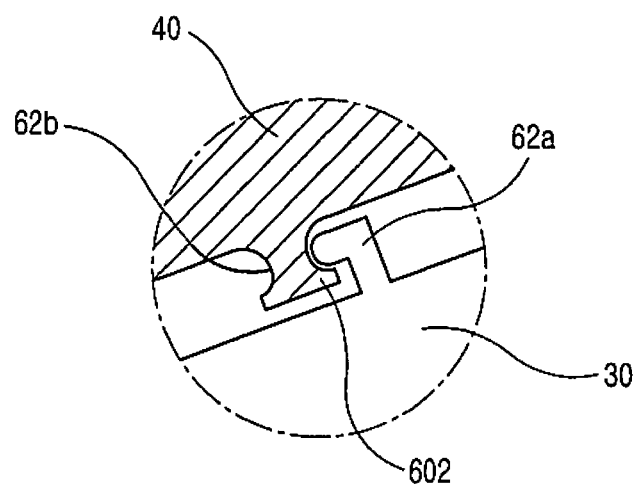
FIG. 7(b) is an enlarged cross-sectional view of a portion as indicated by arrow "A" in FIG. 7(a), illustrating the state that the second locking part is not yet operated.
Figure 7C:
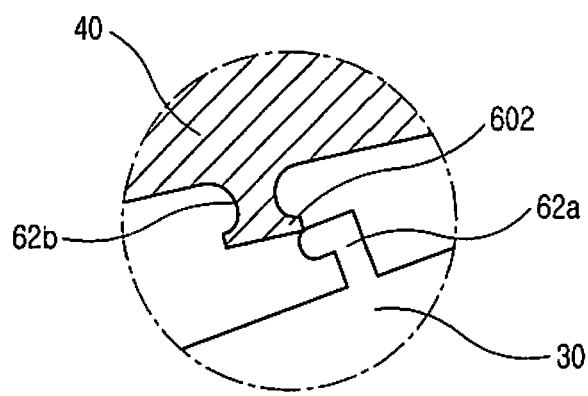
FIG. 7(c) is an enlarged cross-sectional view of the portion as indicated by arrow "A" in FIG. 7(a), illustrating the state that the second locking part is being operated.

FIGS. 7(a) to 7(c) show first and second engaging members 62a and 62b of the second locking part 62. The first engaging member 62a is provided on one side of the second housing 30 to hook the second engaging member 62b. The second engaging member 62b is provided at a location corresponding to the first engaging member 62a on one side of the third housing 40. The second engaging member 62b comes in contact with an outer protrusion A1 of the earphone 1 and is engaged with the latter or released therefrom to fold or unfold the second and third housings 30 and 40 when the second and third housings 30 and 40 are rotated by the elastic member 70. One end of the first engaging member 62a is in the form of the semi-sphere in order to easily disengage from a ridge 602 formed on one end of the second engaging member 62b. The ridge 602 hooked on and released from the first engaging member 62a.

Referring now to FIGS. 3, 4(a), 4(b), and 4(c), the elastic member 70 is composed of first, second and third elastic parts 71, 72 and 73 and a plurality of elastic joints 74. The first elastic part 71 is provided in the first housing 20 and can be folded to or unfolded from the second elastic part 72. The second elastic part 72 is provided in the second housing 30 for applying a stress strain which can return itself to its initial state, to fold to or unfolded from the first elastic part 71 along with the second housing 30. Further, the third elastic part 73 is provided in the third housing 40 for providing a stress strain which can return itself to its initial state, to fold or unfold from the second elastic part 72 along with the third housing 40.

A plurality of elastic joints 74 are provided in the joint parts 50, between the first, second and third elastic parts 71, 72 and 73, to connect the first, second and third elastic parts 71, 72 and 73, and to apply a stress strain to return the first, second and third elastic parts 71, 72 and 73 to their initial states. The elastic joint 74 has a smaller thickness than those of the elastic parts 71, 72 and 73 to provide a stress strain for returning the latter to their initial states.

The first housing 20 is formed with an engaging groove 21 to receive the first locking part 61.

Operations of the apparatus for measuring the biological information and the earphone having the same in accordance with a preferred embodiment of the present invention will be described below with reference to FIGS. 1 through 7.

As shown in FIGS. 1, 2(a), 2(b) and 2(c), the inventive apparatus 10 is provided with the sensor 2 for measuring the biological information. The sensor 2 is preferably a photoplethysmography (PPG) sensor or a transmission-type sensor, which is used to obtain the number of heartbeats, typically during a user's exercise state, measuring an amount of exercise, and checking/removing the stress of the user. The sensor 2 for measuring the biological information includes LED 2a and a Photo Diode (PD) 2b (FIGS. 5(b)-5(c)).

Referring to FIGS. 1 through 7, the apparatus 10 for measuring the biological information includes the first, second and third housings, 20, 30 and 40, a plurality of joint parts 50, a locking part 60, and the elastic member 70. The joint parts 50 are composed of first and second joint parts 51 and 52, respectively. The first joint part 51 is provided between the first and second housings 20 and 30, while the second joint part 52 is provided between the second and third housings 30 and 40.

The elastic member 70 is provided within the respective housings 20, 30 and 40 and the joint parts 50. Here, the elastic member 70 includes the first elastic part 71 provided in the first housing 20, the second elastic part 72 provided in the second housing 30, the third elastic part 73 provided in the third 40, and a plurality of elastic joints 74 provided in the first and second joint parts 51 and 52.

Figure 5A:
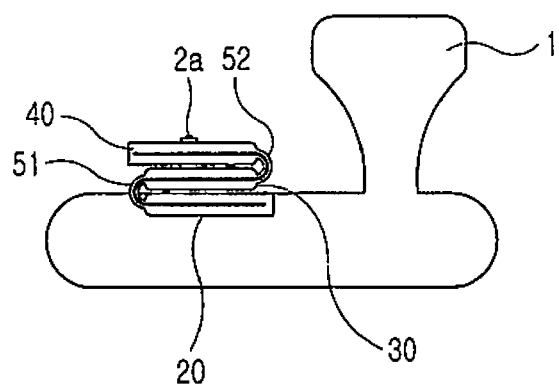
FIG. 5(a) is a side view of the earphone of an embodiment of the present invention in the non-operated state.
Figure 5B:
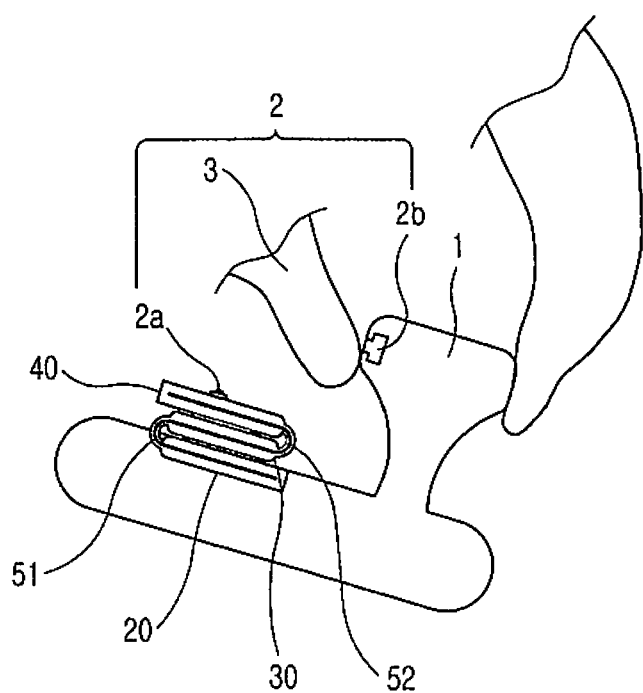
FIG. 5(b) illustrates the earphone of an embodiment of the present invention installed in the user's ear, in the non-operating state.
Figure 5C:
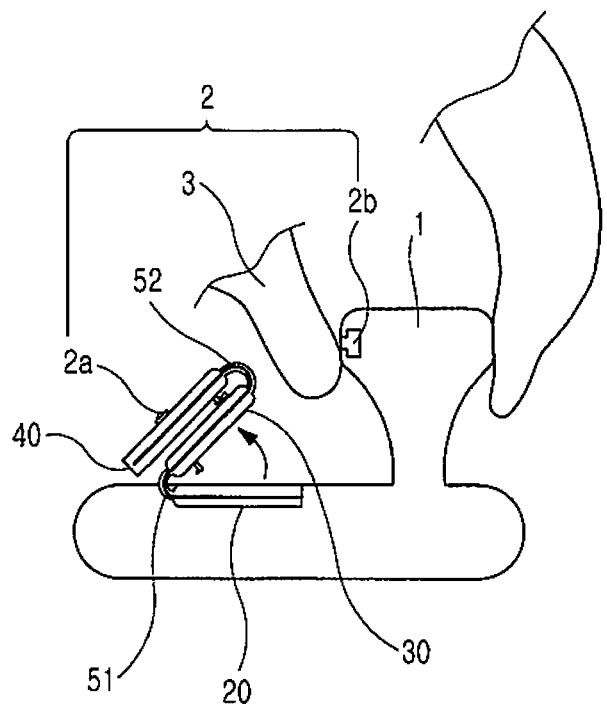
FIG. 5(c) illustrates the earphone installed in the user's ear, at the start of being operated.

It can be noted that the LED 2a of the sensor 2 for measuring the biological information is provided at the third housing 40, while the PD 2b is disposed on the earphone 1 positioned at an opposite side of the user's earlobe 3, as shown in FIGS. 5(b)-5(c).

The first locking part 61 is disposed in the engaging groove 21 formed in the first housing 20, while the second locking part 62 is provided between the second and third housings 30 and 40. In this state, as shown in FIG. 2(a), the first housing 20 of the apparatus 10 is installed in the mounting groove 1a formed in the earphone 1. Then, the user puts the earphone 1 having the inventive apparatus 10 for measuring the biological information into his/her ear, as shown in FIGS. 2(b) and 2(c).

It should be noted here that the earphone 1 is in close contact with the earlobe 3 of the user, and the PD 2b installed within the earphone 1 also makes contact with the earlobe 3. When the user presses both the first and second pressing members 61a and 61b of the first locking part 61, the central portion of a pair of wire latch parts 61d disposed between the first and second pressing members 61a and 61b expands in the opposite direction. Accordingly, the hook part 61c provided at one side of the second housing 30 is released from a pair of wire latch parts 61. At the same time, the second and third housings 30 and 40 are released from their restraint state by the first housing 20, rotating against the first housing 20 to be unfolded.

The second and third elastic parts 72 and 73 received within the second and third housings 30 and 40, then respectively rotate the second and third housings 30 and 40, using the stress strain to return the second and third housings 30 and 40 to their initial states.

Figure 5D:
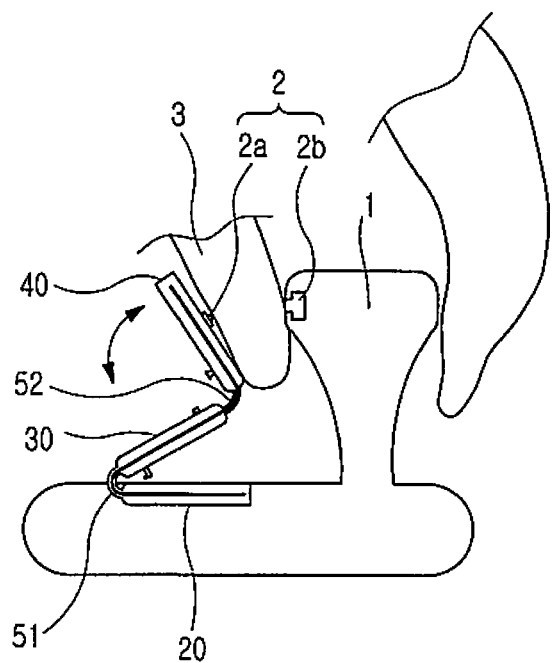
FIG. 5(d) illustrates the earphone in close contact with the earlobe of the user.

Referring to FIGS. 5(c) and 5(d), the elastic joint 74 provided between the second and third elastic parts 72 and 73 and the first and second elastic parts 71 and 72 shows its stress strain with inclination to be returned to its initial state.

As shown in FIGS. 7(a) to 7(c), the second and third housings 30 and 40 rotate around the plurality of joint parts 50 to unfold, and then the third housing 40 comes in contact with the protrusion A1 formed outside of the earphone 1. At this moment, both the first engaging member 62a formed on the second housing 30 and the second engaging member 62b formed on the third housing 40 disengage from each other, allowing the third housing 40 to rotate and unfold from the second housing 30. Here, the third housing 40 is rotated and unfolded by the second joint part 52. In addition, the third elastic part 73 of the elastic member 70 rotates the third housing 40 using its stress strain with inclination to return to its initial state.

Referring to FIG. 5(d), the light emitting diode 2a of the sensor 2 for measuring the biological information provided in the third housing 40 makes contact with the user's earlobe 3 to provide a uniform pressure. The LED 2a is provided at the opposite position from the PD 2b, at opposite sides of the user's earlobe 3. The third housing 40 brings the LED 2a into contact with the user's earlobe 3 with a uniform pressure, regardless of the difference in thickness and length of the earlobe 3, which makes it possible to reduce the signal deviation of the user's biological information and pick up an exact signal in an optimal status.

Meanwhile, the first and second joint parts 51 and 52 have a smaller thickness than those of the respective housings 20, 30 and 40. Similarly, the elastic joint 74 is formed in a smaller thickness than those of the first, second and third elastic parts 71, 72 and 73.

When the elastic joint 74 is manufactured with a cross-sectional thickness, for example 0.5 mm×0.5 mm, the LED 2a of the third housing 40 will contact with the user's earlobe 3 with a force of 0.5 N. Here, the thickness of the elastic joint 74 is not limited to 0.5 mm, but may be less or more than 0.5 mm.

The cross-sectional thickness of the respective elastic parts 71, 72 and 73 and the elastic joint 74 are preferably set more than 2.0 mm×0.5 mm, to increase their inertia values of the second moment.

With different thicknesses for the respective elastic parts 71, 72 and 73 and the elastic joint 74, the inertia value of the second moment due to rotation when the second and third housings 30 and 40 are folded or unfolded can be increased, thereby improving the folding or unfolding operation of the second and third housings 30 and 40.

The disengaging operation of the inventive apparatus 10 for measuring the biological information is now described. Referring to FIGS. 1 through 7a, 7b and 7c, the earphone 1 is first withdrawn from the user's ear. The third housing 40 is folded onto the second housing 30, and the second engaging member 62b of the third housing 40 is hooked and secured to the first engaging member 62a of the second housing 30, whereby the third housing 40 is restrained to the second housing 30.

Figure 6A:
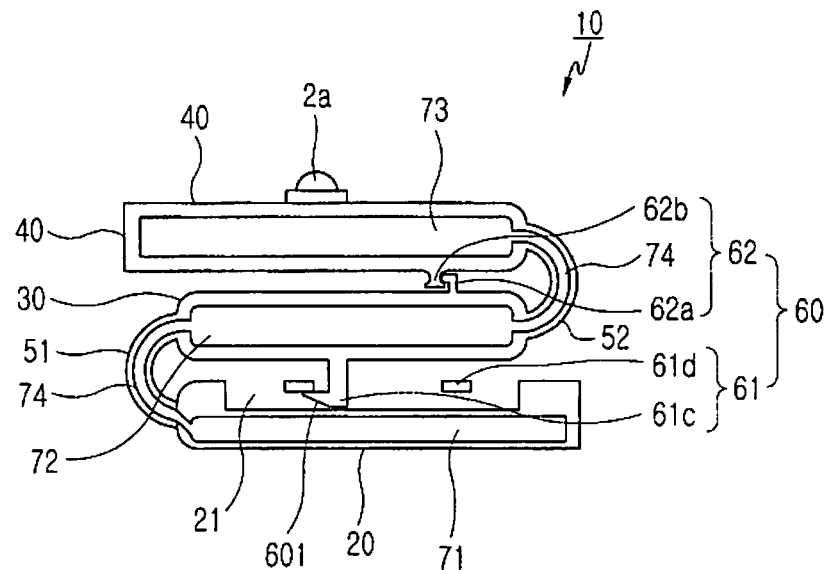
FIG. 6(a) is a side sectional view of an embodiment of the present invention, wherein a first locking part is not yet operated.
Figure 6B:
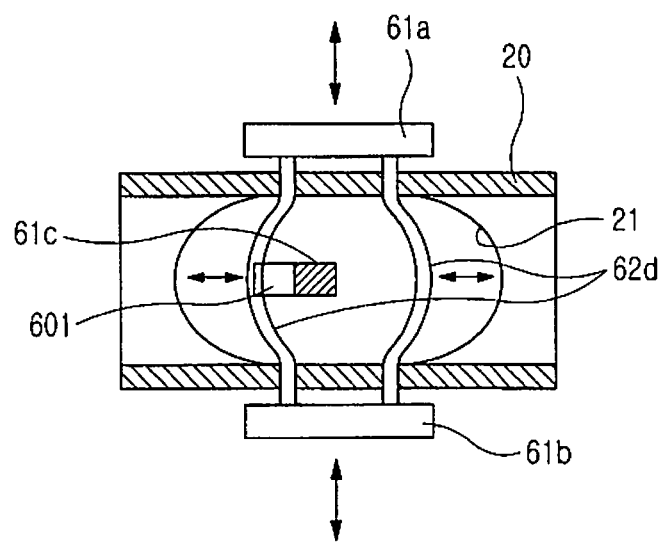
FIG. 6(b) is a top plan view of the embodiment of the present invention, wherein the first locking part is not yet operated.
Figure 6C:
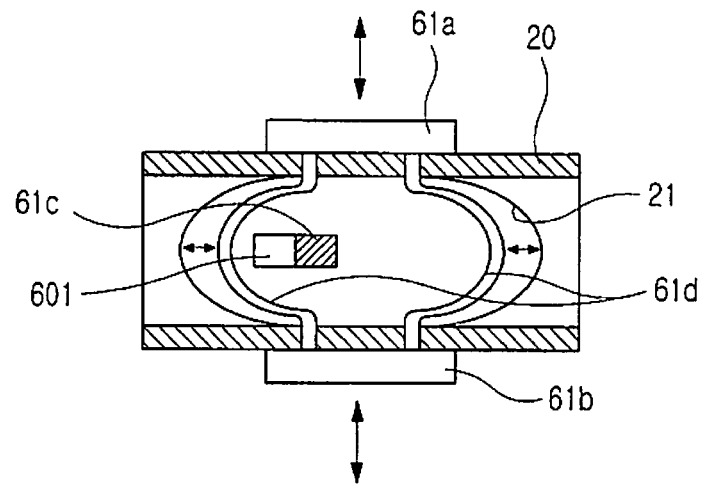
FIG. 6(c) is a top plan view illustrating operation of the first locking part.
Figure 6D:
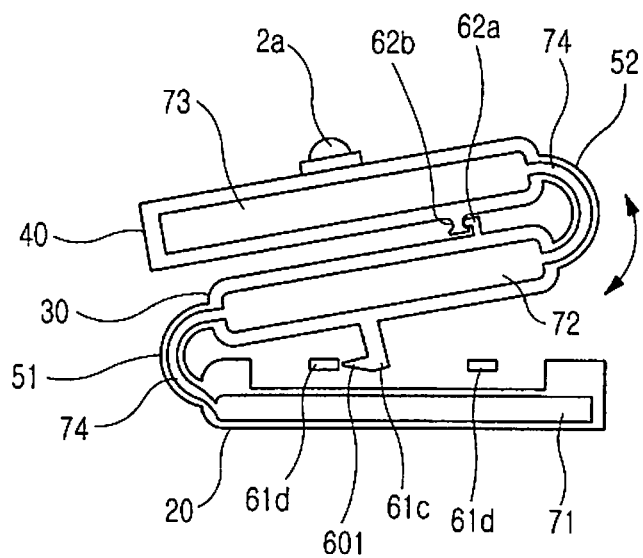
FIG. 6(d) is a side sectional view illustrating operation of the first locking part.

In the above folded state, as shown in FIGS. 6(a) to 6(c), the second and third housings 30 and 40 are folded to each other, and the hook part 61c of the second housing 30 is engaged and secured to a pair of wire latch parts 61d of the first housing 20. Since the hook part 61c is provided with the guide ramp 601, the hook part 61c is smoothly guided along the latter and secured to the wire latch parts 61d when it is coupled with the wire latch parts 61d.

The second and third housings 30 and 40 are restrained together to the first housing 20 in the folded state. At this moment, both the second and third elastic parts 72 and 73 and the elastic joint 74 are folded together with the second and third housings 30 and 40, and further restrained in the folded state.

The embodiments of the apparatus for measuring biological information and the earphone having the same set forth hereinabove have been presented for illustrative purposes only and, therefore, the present invention is not limited to these embodiments and drawings. It will be understood by those skilled in the art that various changes and modifications may be made without departing from the scope of the invention defined in the claims.

What is claimed is:

1. An apparatus for measuring biological information, the apparatus comprising:
   a first housing;
   a second housing foldably connected with the first housing;
   a third housing foldably connected with the second housing and provided with a sensor for measuring the biological information;
   a plurality of joint parts connecting the respective housings about which the housings fold and unfold;
   a locking part provided between the respective housings to restrain the housings in a folded state; and
   an elastic member provided within the respective housings and joint parts that applies a uniform pressure to unfold the respective housings and to contact the sensor against an earlobe.

2. The apparatus of claim 1, wherein the first housing is installed in a mounting groove formed in an earphone.

3. The apparatus of claim 1, wherein the plurality of joint parts include a first elastic joint and a second elastic joint,
   wherein the first elastic joint is provided between the first housing and the second housing, the second elastic joint is provided between the second housing and third housing, and the first elastic joint and second elastic joint have a smaller diameter than their respective housings.

4. The apparatus of claim 1, wherein the elastic member is formed of from a Nitinol material.

5. The apparatus of claim 1, wherein the locking part comprises:
   a first locking part provided between the first housing and the second housing to restrain the first housing and the second housing in the folded state;
   a second locking part provided between the second housing and third housing to restrain the second housing and the third housing in the folded state,
   wherein releasing the first locking part rotates the first housing and the second housing, and then releases and unfolds the second housing and third housing.

6. The apparatus of claim 5, wherein the first locking part comprises:
   first and second pressing members exposed outside of the first housing;
   a hook part provided on one side of the second housing; and
   a pair of wire latch parts provided at a location corresponding to the hook part between the first and second pressing members,
   wherein a central portion of the wire latch parts expands to release the hook part when the first and second pressing members are pressed.

7. The apparatus of claim 6, wherein the hook part includes a guide ramp for contacting one of the wire latch parts.

8. The apparatus of claim 5, wherein the second locking part comprises:
   a first engaging member provided on one side of the second housing; and
   a second engaging member provided at a location corresponding to the first engaging member on one side of the third housing,
   wherein the second engaging member contacts an outer protrusion of an earphone to release the second housing from the third housing, thereby unfolding the second housing from the third housing via rotated by the elastic member.

9. The apparatus of claim 8, wherein one end of the first engaging member formed as a semi-sphere and one end of the second engaging member is formed with a ridge to detachably engage the first engaging member.

10. The apparatus of claim 1, wherein the elastic member comprises:
   a first elastic part provided in the first housing;
   a second elastic part provided in the second housing to unfold the first housing from the second housing;
   a third elastic part provided in the third housing to unfold the second housing from the third housing; and
   first and second elastic joints provided in respective joint parts connecting the first, second and third elastic parts.

11. The apparatus of claim 10, wherein the first and second elastic joints have a diameter smaller than a diameter of the elastic part connected by opposite ends of the elastic joints.

12. The apparatus of claim 5, wherein the first housing is provided with an engaging groove having the first locking part.

* * * * *